(12) United States Patent
Lauffer et al.

(10) Patent No.: US 8,217,056 B2
(45) Date of Patent: Jul. 10, 2012

(54) TRIAZOLOTHIADIAZOLE INHIBITOR OF C-MET PROTEIN KINASE

(75) Inventors: David Lauffer, Stow, MA (US); Pan Li, Lexington, MA (US); Dean Shannon, Milford, MA (US); Jianglin Liang, Needham, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 10 days.

(21) Appl. No.: 12/620,845

(22) Filed: Nov. 18, 2009

(65) Prior Publication Data

US 2010/0234423 A1 Sep. 16, 2010

Related U.S. Application Data

(60) Provisional application No. 61/116,033, filed on Nov. 19, 2008.

(51) Int. Cl.
*C07D 215/12* (2006.01)
*A01N 43/42* (2006.01)
*A61K 31/47* (2006.01)

(52) U.S. Cl. ........ 514/314; 546/176
(58) Field of Classification Search ........ 546/176; 514/314
See application file for complete search history.

(56) References Cited

U.S. PATENT DOCUMENTS

2009/0156594 A1 * 6/2009 Bounaud et al. ........ 514/233.2

FOREIGN PATENT DOCUMENTS

| WO | 2007/064797 | * | 6/2007 |
| WO | 2007/138472 | * | 12/2007 |
| WO | 2008/144767 | * | 11/2008 |

* cited by examiner

*Primary Examiner* — D Seaman
*Assistant Examiner* — Niloofar Rahmani
(74) *Attorney, Agent, or Firm* — Daniel A. Pearson

(57) ABSTRACT

The present invention relates to compound 1, which is useful in the inhibition of c-Met protein kinase. The invention also provides pharmaceutically acceptable compositions comprising Compound 1 and methods of using the compositions in the treatment of proliferative disorders.

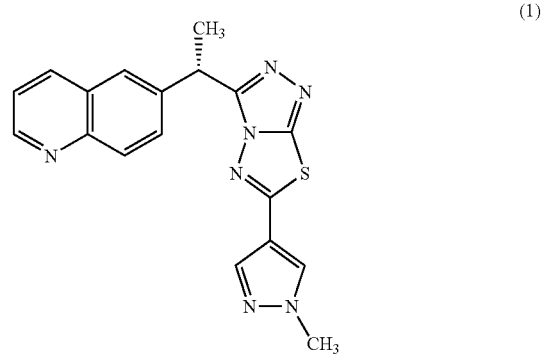

(1)

5 Claims, No Drawings

TRIAZOLOTHIADIAZOLE INHIBITOR OF C-MET PROTEIN KINASE

TECHNICAL FIELD OF THE INVENTION

The present invention relates to selective inhibitors of c-Met. The invention also provides pharmaceutically acceptable compositions comprising a c-Met inhibitor and methods of using the compositions in the treatment of various proliferative disorders.

BACKGROUND OF THE INVENTION

Hepatocyte growth factor (HGF), also known as scatter factor, is a multi-functional growth factor that enhances transformation and tumor development by inducing mitogenesis and cell motility. Further, HGF promotes metastasis by stimulating cell motility and invasion through various signaling pathways. In order to produce cellular effects, HGF must bind to its receptor, c-Met, a receptor tyrosine kinase. c-Met, a widely expressed heterodimeric protein comprising of a 50 kilodalton (kDa) α-subunit and a 145 kDa alpha-subunit (Maggiora et al., *J. Cell Physiol.*, 173:183-186, 1997), is overexpressed in a significant percentage of human cancers and is amplified during the transition between primary tumors and metastasis. The various cancers in which c-Met overexpression is implicated include, but are not limited to, gastric adenocarcinoma, renal cancer, small cell lung carcinoma, colorectal cancer, prostate cancer, brain cancer, liver cancer, pancreatic cancer, and breast cancer. c-Met is also implicated in atherosclerosis and lung fibrosis.

Drug-induced cardiac QT prolongation has recently been recognized to cause adverse or fatal side-effects in many clinical settings. The cardiac potassium channel hERG (human ether-a-go-go-related gene) encodes the α-subunit of the rapid delayed rectifier current $I_{Kr}$ in the heart, which contributes prominently to terminal repolarization in human ventricular myocytes. See Dennis et al., *Biochemical Society Transactions* 35(5):1060-1063 (2007). It has been shown that inhibition of hERG potassium channel can lead to a prolongation of the QT interval, widely considered a critical risk factor for torsades de pointes (TdP) arrhythmia. Thus, overcoming hERG binding has become a major hurdle in drug development.

In addition to an awareness of the possibility of drug-induced QT prolongation, the metabolism of pharmacological agents by cytochrome P450 activity is also important, particularly in therapies that may involve a combination of such agents. The cytochrome P450 enzymes catalyze the oxidation of many therapeutic compounds and have an important role in the extent and duration of drug effects, by catabolizing drugs to inactive metabolites or by bio-activating prodrugs to their active forms. Anti-cancer agents show a wide variation between individuals in response, owing partly to pharmacokinetic variability. See Scipture et al., *Lancet Oncology* 6:780-789 (2005). The most important site of metabolism mediated by cytochrome P450 is the liver, where these enzymes are ubiquitously expressed. There is also evidence that metabolism occurs within tumors and that the presence of these enzymes within tumors can have desirable or adverse effect on the efficacy of chemotherapeutic agents, depending on the isoform present and the cytotoxic agent given. Thus, developing anti-tumor agents that have favorable drug metabolism profiles is also a goal in drug discovery.

Accordingly, there is a great need to develop compounds useful as inhibitors of c-Met protein kinase receptor. In particular, preferred compounds should have high affinity to the c-Met receptor and show functional activity as antagonists, while showing little affinity for other kinase receptors. Furthermore, it is desirable to provide c-Met receptor antagonists that have little or no hERG binding and favorable pharmacokinetic/pharmacodynamic profiles.

SUMMARY OF THE INVENTION

It has been found that 6-((S)-1-(6-(1-methyl-1H-pyrazol-4-yl)-[1,2,4]triazolo[3,4-b][1,3,4]thiadiazol-3-yl)ethyl) quinoline (compound 1) and pharmaceutically acceptable compositions thereof are effective in the inhibition of c-Met. In particular, compound 1 selectively inhibits the activity of c-Met in biological assays, such as, for example, the inhibition of c-Met activity in cells known to over-express this receptor. Further, compound 1 showed minimal hERG-associated potassium channel activity. In addition, compound 1 has suitable pharmacokinetic properties, as evidenced by its behavior in animal models and in vitro assays, particularly in metabolism studies involving cytochrome P450 isozymes.

Accordingly, the invention features the following compound:

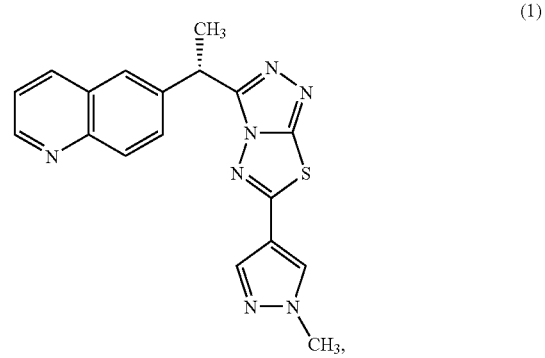

(1)

or a pharmaceutically acceptable salt thereof.

The invention also provides a crystalline form of compound 1.

The invention also provides pharmaceutical compositions that include compound 1, in any form, and a pharmaceutically acceptable carrier, adjuvant, or vehicle. In addition, the invention provides methods of treating or lessening the severity of a proliferative disease, condition, or disorder in a patient that includes the step of administering to the patient a therapeutically effective dose of compound 1, or a pharmaceutical composition thereof.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference.

Description of the Compound of the Invention

In a first aspect, the invention features the following compound:

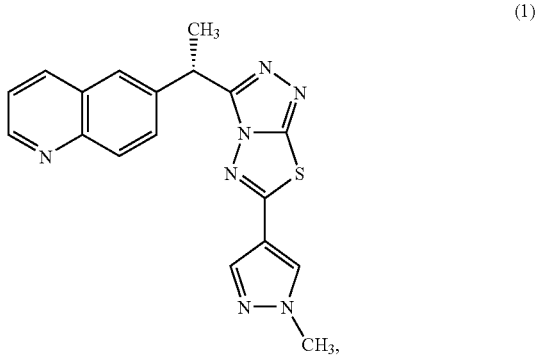

(1)

or a pharmaceutically acceptable salt thereof.

In another aspect, the invention features a crystalline form of compound 1. In one embodiment, crystalline compound 1 is characterized by one or more of the following peaks at 20° C. in an X-ray diffraction pattern (2-theta scale): from 6.2 to 6.4 (e.g., about 6.3), 9.1 to 9.3 (e.g., about 9.2), 11.4 to 11.6 (e.g., about 11.5), 13.2 to 13.4 (e.g., about 13.3), 13.7 to 13.9 (e.g., about 13.8), 14.1 to 14.3 (e.g., about 14.2), 14.7 to 14.9 (e.g., about 14.8), 16.1 to 16.3 (e.g., about 16.2), 18.1 to 18.3 (e.g., about 18.2), 18.6 to 18.8 (e.g., about 18.7), and 19.7 to 19.9 (e.g., about 19.8).

Compositions, Formulations, and Administration of Compounds of the Invention

In another aspect, the invention provides a composition comprising compound 1 or a pharmaceutically acceptable derivative thereof and a pharmaceutically acceptable carrier, adjuvant, or vehicle. In one embodiment, the amount of compound in a composition of this invention is such that is effective to measurably inhibit c-Met in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

It will also be appreciated that compound 1 can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, compound 1 as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 66:1-19, 1977, which is incorporated herein by reference. Pharmaceutically acceptable salts of compound 1 include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with compound 1, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of compound 1 include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of compound 1, it is often desirable to slow the absorption of this compound from subcutaneous or intramuscular injection. This may be accomplished by the use of a liquid suspension of crystalline or amorphous material with poor water solubility. The rate of absorption of compound 1 then depends upon its rate of dissolution that, in turn, may depend upon crystal size and crystalline form. Alternatively, dissolving or suspending compound 1 in an oil vehicle accomplishes delayed absorption of a parenterally administered compound form. Injectable depot forms are made by forming microencapsule matrices of compound 1 in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping compound 1 in liposomes or microemulsions that are compatible with body tissues.

Compositions for rectal or vaginal administration are preferably suppositories which can be prepared by mixing compound 1 with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of compound 1 include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of compound 1 to the body. Such dosage forms can be made by dissolving or dispensing compound 1 in the proper medium. Absorption enhancers can also be used to increase the flux of compound 1 across the skin. The rate can be controlled by either providing a rate controlling membrane or by dispersing compound 1 in a polymer matrix or gel.

Compound 1 is preferably formulated in dosage unit form for ease of administration and uniformity of dosage. The expression "dosage unit form" as used herein refers to a physically discrete unit of agent appropriate for the patient to be treated. It will be understood, however, that the total daily usage of compound 1 and compositions comprising compound 1 will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of compound 1 that may be combined with the carrier materials to produce a composition in a single dosage form will vary depending upon the host treated, the particular mode of administration. Preferably, the compositions should be formulated so that a dosage of from 0.01 to 100 mg/kg body weight/day of the inhibitor can be administered to a patient receiving these compositions. In one example, compositions are formulated such that the dosage of compound 1 is from 5 to 30 mg/kg body weight/day.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated." Examples of additional therapeutic agents are provided infra.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of Compound 1 and Compositions Comprising Compound 1

According to one embodiment, the invention relates to a method of inhibiting c-Met protein kinase activity in a biological sample comprising the step of contacting said biological sample with compound 1, or a composition comprising said compound. The term "biological sample," as used herein, means a sample outside a living organism and includes, without limitation, cell cultures or extracts thereof biopsied material obtained from a mammal or extracts thereof and blood, saliva, urine, feces, semen, tears, or other body fluids or extracts thereof. Inhibition of kinase activity in a biological sample is useful for a variety of purposes known to one of skill in the art. Examples of such purposes include, but are not limited to, biological specimen storage and biological assays. In one embodiment, the method of inhibiting kinase activity in a biological sample is limited to non-therapeutic methods.

The term "c-Met" is synonymous with "c-MET," "cMet", "MET", "Met" or other designations known to one skilled in the art.

According to another embodiment, the invention relates to a method of inhibiting c-Met kinase activity in a patient comprising the step of administering to said patient compound 1, or a composition comprising said compound.

The term "c-Met-mediated disease" or "c-Met-mediated condition", as used herein, means any disease state or other deleterious condition in which c-Met is known to play a role. The terms "c-Met-mediated disease" or "c-Met-mediated condition" also mean those diseases or conditions that are alleviated by treatment with a c-Met inhibitor. Such conditions include, without limitation, renal, gastric, colon, brain, breast, prostate, liver, pancreatic, or lung cancer, glioblastoma, atherosclerosis, or lung fibrosis.

In one aspect, the present invention features a method treating a proliferative disorder in a patient comprising the step of administering to the patient a therapeutically effective dose of compound 1 or a composition comprising compound 1.

According to one embodiment, the proliferative disorder is cancer, such as, for example, renal, gastric, colon, brain, breast, liver, prostate, and lung cancer, or a glioblastoma.

In another embodiment, the present invention relates to a method of treating or lessening the severity of hepatocellular carcinoma in a patient in need thereof, comprising administering to said patient compound 1 or composition thereof.

In another embodiment, the proliferative disorder is polycythemia vera, essential thrombocythemia, chronic idiopathic myelofibrosis, myeloid metaplasia with myelofibrosis, chronic myeloid leukemia (CML), chronic myelomonocytic leukemia, chronic eosinophilic leukemia, hypereosinophilic syndrome, systematic mast cell disease, atypical CML, or juvenile myelomonocytic leukemia.

In another embodiment, the proliferative disorder is atherosclerosis or lung fibrosis.

Another aspect of the present invention relates to a method of inhibiting tumor metastasis in a patient in need thereof, comprising administering to said patient compound 1 or a composition thereof.

Depending upon the particular condition, or disease, to be treated, additional therapeutic agents that are normally administered to treat that condition may also be present in the compositions of this invention. As used herein, additional therapeutic agents that are normally administered to treat a particular disease, or condition, are known as "appropriate for the disease, or condition, being treated".

In one embodiment, chemotherapeutic agents or other antiproliferative agents may be combined with compound 1 to treat proliferative diseases and cancer. Examples of known chemotherapeutic agents include, but are not limited to, alkylating agents, such as, for example, cyclophosphamide, lomustine, busulfan procarbazine, ifosfamide, altretamine, melphalan, estramustine phosphate, hexamethylmelamine, mechlorethamine, thiotepa, streptozocin, chlorambucil, temozolomide, dacarbazine, semustine, or carmustine; platinum agents, such as, for example, cisplatin, carboplatinum, oxaliplatin, ZD-0473 (AnorMED), spiroplatinum, lobaplatin (Aeterna), carboxyphthalatoplatinum, satraplatin (Johnson Matthey), tetraplatin BBR-3464, (Hoffmann-La Roche), ormiplatin, SM-11355 (Sumitomo), iproplatin, or AP-5280 (Access); antimetabolites, such as, for example, azacytidine, tomudex, gemcitabine, trimetrexate, capecitabine, deoxycoformycin, 5-fluorouracil, fludarabine, floxuridine, pentostatin, 2-chlorodeoxyadenosine, raltitrexed, 6-mercaptopurine, hydroxyurea, 6-thioguanine, decitabine (SuperGen), cytarabin, clofarabine (Bioenvision), 2-fluorodeoxy cytidine, irofulven (MGI Pharma), methotrexate, DMDC (Hoffmann-La Roche), idatrexate, or ethynylcytidine (Taiho); topoisomerase inhibitors, such as, for example, amsacrine, rubitecan (SuperGen), epirubicin, exatecan mesylate (Daiichi), etoposide, quinamed (ChemGenex), teniposide, mitoxantrone, gimatecan (Sigma-Tau), irinotecan (CPT-11), diflomotecan (Beaufour-Ipsen), 7-ethyl-10-hydroxy-camptothecin, TAS-103 (Taiho), topotecan, elsamitrucin (Spectrum), dexrazoxanet (TopoTarget), J-107088 (Merck & Co), pixantrone (Novuspharma), BNP-1350 (BioNumerik), rebeccamycin analogue (Exelixis), CKD-602 (Chong Kun Dang), BBR-3576 (Novuspharma), or KW-2170 (Kyowa Hakko); antitumor antibiotics, such as, for example, dactinomycin (actinomycin D), amonafide, doxorubicin (adriamycin), azonafide, deoxyrubicin, anthrapyrazole, valrubicin, oxantrazole, daunorubicin (daunomycin), losoxantrone, epirubicin, bleomycin, sulfate (blenoxane), therarubicin, bleomycinic acid, idarubicin, bleomycin A, rubidazone, bleomycin B, plicamycinp, mitomycin C, porfiromycin, MEN-10755 (Menarini), cyanomorpholinodoxorubicin, GPX-100 (Gem Pharmaceuticals), or mitoxantrone (novantrone), antimitotic agents, such as, for example, paclitaxel, SB 408075 (GlaxoSmithKline), docetaxel, E7010 (Abbott), colchicines, PG-TXL (Cell Therapeutics), vinblastine, IDN 5109 (Bayer), vincristine A, 105972 (Abbott), vinorelbine, A 204197 (Abbott), vindesine, LU 223651 (BASF), dolastatin 10 (NCI), D 24851 (ASTAMedica), rhizoxin (Fujisawa), ER-86526 (Eisai), mivobulin (Warner-Lambert), combretastatin A4 (BMS), cemadotin (BASF), isohomohalichondrin-B (PharmaMar), RPR 109881A (Aventis), ZD 6126 (AstraZeneca), TXD 258 (Aventis), PEG-paclitaxel (Enzon,) epothilone B (Novartis), AZ10992 (Asahi), T 900607 (Tularik), IDN-5109 (Indena), T 138067 (Tularik), AVLB (Prescient NeuroPharma), cryptophycin 52 (Eli Lilly), azaepothilone B (BMS), vinflunine (Fabre), BNP-7787 (BioNumerik), auristatin PE (Teikoku Hormone), CA-4 prodrug (OXiGENE), BMS 247550 (BMS), dolastatin-10 (NIH), BMS 184476 (BMS), CA-4 (OXiGENE), BMS 188797 (BMS), or taxoprexin (Protarga); aromatase inhibitors, such as, for example, aminoglutethimide, exemestane, letrozole, atamestane (BioMedicines), anastrazole, YM-511 (Yamanouchi), or formestane; thymidylate synthase inhibitors, such as, for example, pemetrexed (Eli Lilly), nolatrexed (Eximias), ZD-9331 (BTG), or CoFactor™ (BioKeys); DNA antagonists, such as, for example, trabectedin (PharmaMar), mafosfamide (Baxter International), glufosfamide (Baxter International), apaziquone (Spectrum Pharmaceuticals), albumin+$^{32}$P (Isotope Solutions), 06 benzyl guanine (Paligent), thymectacin (NewBiotics), or edotreotide (Novartis); farnesyltransferase inhibitors, such as, for example, arglabin (NuOncology Labs), tipifarnib (Johnson & Johnson), lonafarnib (Schering-Plough), perillyl alcohol (DOR BioPharma), or BAY-43-9006 (Bayer); Pump inhibitors, such as, for example, CBT-1 (CBA Pharma), zosuquidar trihydrochloride (Eli Lilly), tariquidar (Xenova), biricodar dicitrate (Vertex), or MS-209 (Schering AG); Histone acetyltransferase inhibitors, such as, for example, tacedinaline (Pfizer), pivaloyloxymethyl butyrate (Titan), SAHA (Aton Pharma), depsipeptide (Fujisawa), or MS-275 (Schering AG); Metalloproteinase inhibitors, such as, for example, Neovastat (Aeterna Laboratories), CMT-3 (CollaGenex), marimastat (British Biotech), or BMS-275291 (Celltech); ribonucleoside reductase inhibitors, such as, for example, gallium maltolate (Titan), tezacitabine (Aventis), triapine (Vion), or didox (Molecules for Health); TNF alpha agonists/antagonists, such as, for example, virulizin (Lorus Therapeutics), revimid (Celgene), CDC-394 (Celgene), entanercept (Immunex Corp.), infliximab (Centocor, Inc.), or adalimumab (Abbott Laboratories); endothelin A receptor antagonists, such as, for example, atrasentan (Abbott) YM-598 (Yamanouchi) or ZD-4054 (AstraZeneca); retinoic acid receptor agonists, such as, for example, fenretinide (Johnson & Johnson) alitretinoin (Ligand) or LGD-1550 (Ligand); immuno-modulators, such as, for example, interferon dexosome therapy (Anosys), oncophage (Antigenics), pentrix (Australian Cancer Technology), GMK (Progenics), ISF-154 (Tragen), adenocarcinoma vaccine (Biomira), cancer vaccine (Intercell), CTP-37 (AVI BioPharma), norelin (Biostar), IRX-2 (Immuno-Rx), BLP-25 (Biomira), PEP-005 (Peplin Biotech), MGV (Progenies), synchrovax vaccines (CTL Immuno), beta-alethine (Dovetail), melanoma vaccine (CTL Immuno), CLL therapy (Vasogen), or p21 RAS vaccine (GemVax); hormonal and antihormonal agents, such as, for example, estrogens, prednisone, conjugated estrogens, methylprednisolone, ethinyl estradiol, prednisolone, chlortrianisen, aminoglutethimide, idenestrol, leuprolide, hydroxyprogesterone caproate, goserelin, medroxyprogesterone, leuporelin, testosterone, bicalutamide, testosterone propionate, fluoxymesterone, flutamide, methyltestosterone, octreotide, diethylstilbestrol, nilutamide, megestrol, mitotane, tamoxifen, P-04 (Novogen), toremofine, 2-methoxyestradiol (EntreMed), dexamethasone, or arzoxifene (Eli Lilly); photodynamic agents, such as, for example, talaporfin (Light Sciences), Pd-bacteriopheophorbide (Yeda), Theralux (Theratechnologies), lutetium texaphyrin (Pharmacyclics), motexafin gadolinium (Pharmacyclics), or hypericin; and tyrosine kinase inhibitors, such as, for example, imatinib (Novartis), kahalide F (PharmaMar), leflunomide (Sugen/Pharmacia), CEP-701 (Cephalon), ZD1839 (AstraZeneca), CEP-751 (Cephalon), erlotinib (Oncogene Science), MLN518 (Millenium), canertinib (Pfizer), PKC412 (Novartis), squalamine (Genaera), phenoxodiol, SU5416 (Pharmacia), trastuzumab (Genentech), SU6668 (Pharmacia), C225 (ImClone), ZD4190 (AstraZeneca), rhu-Mab (Genentech), ZD6474 (AstraZeneca), MDX-H210 (Medarex), vatalanib (Novartis), 2C4 (Genentech), PKI166 (Novartis), MDX-447 (Medarex), GW2016 (GlaxoSmithKline), ABX-EGF (Abgenix), EKB-509 (Wyeth), IMC-1C11 (ImClone), or EKB-569 (Wyeth).

Those additional agents may be administered separately from the compound 1-containing composition, as part of a multiple dosage regimen. Alternatively, those agents may be part of a single dosage form, mixed together with compound 1 in a single composition. If administered as part of a multiple dosage regime, the two active agents may be submitted simultaneously, sequentially or within a period of time from one another normally within five hours from one another.

The amount of both, compound 1 and the additional therapeutic agent (in those compositions which comprise an additional therapeutic agent as described above)) that may be combined with the carrier materials to produce a single dosage form will vary depending upon the host treated and the particular mode of administration. Preferably, the compositions of this invention should be formulated so that a dosage of between 0.01-100 mg/kg body weight/day of compound 1 can be administered. In one example, compositions are formulated such that the dosage of compound 1 is from 5 to 30 mg/kg body weight/day.

In those compositions that comprise an additional therapeutic agent, that additional therapeutic agent and compound 1 may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Compound 1, or pharmaceutical compositions thereof, may also be incorporated into compositions for coating an implantable medical device, such as prostheses, artificial valves, vascular grafts, stents and catheters. Vascular stents, for example, have been used to overcome restenosis (renarrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Implantable devices coated with compound 1 are another embodiment of the present invention.

In order that the invention described herein may be more fully understood, the following examples are set forth. It should be understood that these examples are for illustrative purposes only and are not to be construed as limiting this invention in any manner.

Unless otherwise indicated, the HPLC method utilized to obtain the reported retention time is as follows: column: Zorbax SB C18 column, 3.0×150 mm; gradient: 10-90% acetonitrile/water (0.1% TFA), 5 minutes; flow rate: 1.0 mL/minute; and detection: 254 & 214 nm.

Synthetic Procedure

Compound 1 may be prepared by the following method, as shown in Scheme 1 and exemplified in Example 1.

Scheme 1

Preparation of Compound 1

The following definitions describe terms and abbreviations used herein:
Brine a saturated solution of NaCl in water
BSA bovine serum albumin
DMSO dimethylsulfoxide
ESMS electrospray mass spectrometry
EtOAc ethyl acetate
EtOH ethyl alcohol
FB free base
HPLC high performance liquid chromatography
LCMS liquid chromatography-mass spectrometry
Me methyl
MeOH methanol
Ph phenyl
RT room temperature
TCA trichloroacetic acid
THF tetrahydrofuran
TFA trifluoacetic acid As used herein, other abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997, herein incorporated in its entirety by reference.

As used herein, the term "$R_f$(min)" refers to the HPLC retention time, in minutes, associated with a compound.

EXAMPLE 1

Preparation of 6-((S)-1-(6-(1-methyl-1H-pyrazol-4-yl)-[1,2,4]triazolo[3,4-b][1,3,4]thiadiazol-3-yl)ethyl) quinoline (compound 1)

As shown in step i of Scheme 1, concentrated sulfuric acid (206 mL, 3.868 mol) was added dropwise to a solution of 2-(quinolin-6-yl)acetic acid (compound 1001, 658.2 g, 3.516 mol, Okeanos Tech Co., Cat. No. OK-J-05024) in 6.5 liters of methanol. During the addition, a slight exotherm was observed. After the addition was complete, the reaction was stirred at reflux for 4 hours. After cooling, the volatiles were removed under reduced pressure, the resulting residue was diluted with 4 liters of ethyl acetate, cooled in an ice bath, treated with 2N NaOH (2.1 liters, 1.2 equiv.) until a pH of 4 was achieved, and then treated with saturated sodium bicarbonate until a pH of 8 was achieved. The layers were separated and the aqueous layer extracted twice with ethyl acetate. The combined organics were washed with saturated sodium bicarbonate, washed with water, washed with brine, dried over anhydrous $MgSO_4$, filtered, and evaporated under reduced pressure to afford methyl 2-(quinolin-6-yl)acetate as a clear brown oil (compound 1002, 696.8 g, 98% yield): ESMS (M+1), 202.14; $^1$H NMR (300.0 MHz, DMSO-$d_6$) δ 8.90 (1H, dd, J=1.7, 4.2 Hz), 8.14-8.10 (1H, m), 8.08 (1H, d, J=8.7 Hz), 7.72 (1H, d, J=1.4 Hz), 7.65 (1H, dd, J=2.0, 8.7 Hz), 7.40 (1H, dd, J=4.2, 8.3 Hz), 3.83 (2H, s), 3.73 (3H, s).

As shown in step ii of Scheme 1, methyl 2-(quinolin-6-yl) acetate (82 g, 407.5 mmol), paraformaldehyde (25.89 g, 862.1 mmol), $K_2CO_3$ (101.4 g, 733.5 mmol), and hexadecyl (trimethyl)ammonium hydrogen sulfate (15.55 g, 40.75 mmol) were taken up in toluene (1.6 liters) and refluxed for 2 hours until the starting material was completely consumed, as monitored by HPLC. The reaction mixture was cooled down using an ice-water bath and filtered through diatomaceous earth. The filtrate was washed with 1 liter of water and the organic layer dried over anhydrous sodium sulfate, filtered, and evaporated under reduced pressure to afford methyl 2-(quinolin-6-yl)acrylate as a clear colorless oil (75.0 g). This material was used immediately without further purification in the next reaction.

Accordingly, as shown in step iii of Scheme 1, methyl 2-(quinolin-6-yl)acrylate (75.0 g) was dissolved in a solution containing sodium hydroxide (65.2 g, 1.63 mol) in 1.1 liters of tetrahydrofuran and 1.1 liters of water. The reaction was stirred at room temperature overnight. The organic layer was partitioned off and the aqueous layer washed with 500 mL of toluene. The aqueous layer was then cooled with an ice bath and acidified by dropwise addition of concentrated HCl until a pH of 4.5 was achieved (about 125 mL of conc. HCl, 1.508 mol), resulting in a white precipitate. After the addition was complete, the reaction was stirred for an additional 0.5 hour at 5° C. The precipitate was collected by vacuum filtration, washed with water, washed with methyl t-butyl ether, and dried under vacuum to afford 2-(quinolin-6-yl)acrylic acid (compound 1003, 36.2 g): ESMS (M+1), 200.06; $^1$H NMR (300.0 MHz, DMSO-$d_6$) δ 13.01 (1H, s), 8.91 (1H, dd, J=1.8, 4.2 Hz), 8.40 (1H, d, J=7.5 Hz), 8.07 (1H, d, J=1.8 Hz), 8.01 (1H, d, J=8.7 Hz), 7.84 (1H, dd, J=1.9, 8.9 Hz), 7.55 (1H, dd, J=1.2, 8.4 Hz), 6.39 (1H, d, J=0.9 Hz), 6.17 (1H, d, J=0.9 Hz).

As shown in step iv of Scheme 1,2-(quinolin-6-yl)acrylic acid (84.5 g, 424 mmol), methanol (422 mL), and triethylamine (118 mL) was placed in a 2 liter glass cylindrical vessel under nitrogen. The solution was deoxygenated by bubbling a stream of nitrogen through the solution for 1 hour. Dichloro[(S)-(−)-2,2'-bis(diphenylphopino)-1,1'-binaphthyl]ruthenium (II) (710 mg, 0.848 mmol) was added to the solution and the glass vessel was placed into a stainless steel Parr high pressure reactor and stirred 16 hours at room temperature under 1000 psi of hydrogen gas. After this time, the hydrogen atmosphere was removed, a ruthenium scavenger (Silicycle®-DMT, 8.78 g, 6 equiv.) added, and the mixture stirred at room temperature an additional 16 hours. The mixture was filtered and the filtrate concentrated under reduced pressure to afford a brown viscous oil, which was dissolved in 170 mL of water. The aqueous solution was acidified by the dropwise addition of 6 N HCl until a pH of 4-5 was achieved. The resulting precipitate was collected by vacuum filtration, washed with water, washed with methyl t-butyl ether, and dried in a vacuum oven at 50° C. overnight to afford (S)-2-(quinolin-6-yl)propanoic acid (compound 1004, 68.6 g) as a reddish brown solid: ESMS (M+1), 202.19; $^1$H NMR (300.0 MHz, DMSO-$d_6$) δ 12.42 (1H, br.s), 8.87 (1H, dd, J=1.7, 4.2 Hz), 8.35 (1H, d, J=7.6 Hz), 7.98 (1H, d, J=8.7 Hz), 7.87 (1H, d, J=1.7 Hz), 7.71 (1H, dd, J=2.0, 8.7 Hz), 7.52 (1H, dd, J=4.2, 8.3 Hz), 3.91 (1H, q, J=7.1 Hz), 1.48 (3H, d, J=7.1 Hz). A second crop of crystalline product was collected (11.5 g) for an overall yield of 94%. Analysis by supercritical fluid chromatography (SFC) using a chiral Whelk-O® column eluting with (30% MeOH/0.2% diethylamine) in $CO_2$ showed 91% enantiomeric excess (ee) of the desired S-isomer.

As shown in step v of Scheme 1, (S)-2-(quinolin-6-yl) propanoic acid (50 g, 248.5 mmol) and 1,3-diaminothiourea (29.02 g, 273.4 mmol) were suspended in a mixture of tetramethylene sulfone (sulfolane, 38 mL) and water (57 mL). Methane sulfonic acid (35.5 ml, 546.7 mmol) was added to the mixture, whereupon all solids dissolved. The reaction temperature was slowly increased to 90° C. and the reaction was heated at 90° C. for 40 hours, at which time a 68% conversion of starting material to product was observed by HPLC analysis. The reaction mixture was cooled in an ice bath and water (75 mL) was added, followed by the careful addition of saturated sodium bicarbonate (500 mL) until a pH 8 was achieved. The resulting fine purple precipitate was collected by vacuum filtration, washed with water, saturated sodium bicarbonate, water, and methyl t-butyl ether, respectively. The product was dried in a vacuum oven at 55° C. for 2 days to afford 6-((S)-1-(5-mercapto-4-amino-4H-1,2,4-triazol-3-yl)ethyl)quinoline (compound 1005, 43 g): ESMS (M+1), 272.09; $^1$H NMR (300.0 MHz, DMSO-$d_6$) δ 13.65 (1H, br s), 8.86 (1H, dd, J=1.8, 8.4 Hz), 8.34 (1H, d, J=7.5 Hz), 7.98 (1H, d, J=8.7 Hz), 7.84 (1H, dd, J=1.7, 13.7 Hz), 7.82 (1H, d, J=1.5 Hz), 7.70 (1H, dd, J=1.8, 8.7 Hz), 7.50 (1H, dd, J=1.8, 8.7 Hz), 5.44 (2H, s), 4.57 (1H, q, J=7.2 Hz), 1.65 (3H, d, J=7.2 Hz). The product was 92% pure by $^1$H NMR analysis, with the major impurities being compound 1004 and sulfolane. Chiral HPLC analysis showed 92% ee (ChiralPak® AD-H, 70% i-propanol/hexanes; retention time: 4.98 min for S-enantiomer, 12.33 min for R-enantiomer). The product was used as is in the next step without further purification.

Compound 1004 could be recovered from the aqueous filtrate by adjusting its pH to 5, collecting any precipitated material, and extracting the remaining filtrate with ethyl acetate (3 times). The combined organics were dried over anhydrous sodium sulfate, filtered, and evaporated under reduced pressure to afford a dark oil, which was taken up in 90 mL of ethyl acetate and heated to reflux for 0.5 hour. Cooling resulted in additional precipitate which, when combined with the previously collected precipitate, resulted in the recovery of compound 1004 as white solid (7 g).

As shown in step vi of Scheme 1,6-((S)-1-(5-mercapto-4-amino-4H-1,2,4-triazol-3-yl)ethyl)quinoline (123.0 g, 453.3 mmol) and 1-methyl-1H-pyrazole-4-carboxylic acid (60.03 g, 476.0 mmol, Aldrich Chemical Co. Cat. No. 682063) were dissolved in $POCl_3$ (1.23 liters) and sulfolane (246 mL) and stirred for 18 hours at 83° C. The volatiles were evaporated under reduced pressure and the residue additionally azeotroped with toluene twice more under reduced pressure. The resulting oil was slowly poured into stirring ice-water and the aqueous solution was extracted with dichloromethane to remove any residual sulfolane. The aqueous solution was treated with saturated sodium bicarbonate (3.2 liters) until a pH of 7 was achieved. The resulting oil was decanted off and dissolved in a small amount of methanol, with the remaining aqueous layer extracted with dichloromethane (4 times). The combined organic extracts and the methanol solution of the oil were combined and washed with saturated sodium bicarbonate, water, and brine, respectively. The organics were dried over anhydrous $MgSO_4$, filtered, and evaporated under reduced pressure to afford the crude product as a thick brown oil. The product was purified by silica gel chromatography, eluting with a gradient of dichloromethane to 5% methanol in dichloromethane. Fractions containing product were evaporated under reduced pressure to provide a yellow solid, which was further purified by crystallization from dichloromethane (300 mL) and methyl t-butyl ether (300 mL) to provide 6-((S)-1-(6-(1-methyl-1H-pyrazol-4-yl)-[1,2,4]triazolo[3,4- b][1,3,4]thiadiazol-3-yl)ethyl)quinoline (compound 1, 62.8 g, 38% yield) as a light yellow solid: ESMS (M+1), 362.38; $^1$H NMR (300.0 MHz, DMSO-$d_6$) δ 8.87 (1H, dd, J=1.7, 4.3 Hz); 8.54 (1H, s); 8.36 (1H, br. d, J=8.3 Hz); 8.03 (1H, s); 8.00 (1H, d, J=8.3 Hz); 7.92 (1H, d, J=1.7 Hz); 7.80 (1H, dd, J=1.9, 8.8 Hz); 7.52 (1H, dd, J=4.2, 8.2 Hz); 4.90 (1H, q, J=7.2 Hz); 3.90 (3H, s); 1.86 (3H, d, J=7.2 Hz). Chiral HPLC analysis showed 99+% ee (ChiralPak® AD-H, 70% ethanol/hexanes.

EXAMPLE 2

Crystallization of Compound 1 (Free Base)

To compound 1 (906 mg) was added 40 mL of acetonitrile and 10 mL of methanol. The solid was dissolved on a hot water bath at about 90° C. The solution was filtered off and was allowed to slowly evaporate at room temperature for 4 hours. Crystals gradually precipitated. The mother liquor was decanted and the solid was dried at room temperature under 4 mm Hg vacuum over night.

About 10 mg of compound 1, crystalline free base (FB), was loaded into a vial with a magnetic stir bar. About 150 µL of solvent were added to each vial. If compound 1 dissolved completely, more solid was added to the vial and stirring of the resulting slurry was continued at room temperature. The 4 day solution was filtered off using centrifuge filters and diluted in methanol to obtain solubility data by HPLC analysis. The results of the solubility study are shown in Table 1. X-ray diffraction data of the crystals in the slurry were collected after 4 and 14 days. All forms that remained crystalline exhibited an X-ray diffraction pattern that included the following peaks (theta scale): from 6.2 to 6.4 (e.g., about 6.3), 9.1 to 9.3 (e.g., about 9.2), 11.4 to 11.6 (e.g., about 11.5), 13.2 to 13.4 (e.g., about 13.3), 13.7 to 13.9 (e.g., about 13.8), 14.1 to 14.3 (e.g., about 14.2), 14.7 to 14.9 (e.g., about 14.8), 16.1 to 16.3 (e.g., about 16.2), 18.1 to 18.3 (e.g., about 18.2), 18.6 to 18.8 (e.g., about 18.7), and 19.7 to 19.9 (e.g., about 19.8).

TABLE 1

Solubility of compound 1 in different solvents as measured by HPLC

| Solvent | Dilution factor | AUC | Conc. FB (mg/mL) |
|---|---|---|---|
| water | 200 | 50.93 | 0.15 |
| Nitromethane | 2000 | 1090.09 | 44.43 |
| Acetonitrile | 2000 | 250.84 | 9.76 |
| Methanol | 2000 | 1008.12 | 41.04 |
| Ethanol | 200 | 10197.90 | 42.06 |
| Acetone | 200 | 3467.41 | 14.26 |
| IPA | 200 | 1932.85 | 7.92 |
| MEK | 200 | 3461.35 | 14.24 |
| 2-Methyl THF | 200 | 2201.18 | 9.03 |
| DME | 200 | 3901.62 | 16.06 |
| EtOAc | 200 | 1767.01 | 7.24 |
| DCM | 2000 | 2833.34 | 116.43 |
| MTBE | 200 | 87.41 | 0.30 |
| Cumene | 200 | 625.29 | 2.52 |
| Dioxane | 200 | 8915.48 | 36.76 |
| Cyclohexane | 200 | 2.64 | −0.05 |
| Glycerol | 200 | 182.30 | 0.69 |
| Diiodomethane | 2000 | 1974.38 | 80.95 |
| Ethylene Glycol | 200 | 8570.55 | 35.34 |
| Benzyl Alcohol | 2000 | 8767.90 | 361.55 |
| DMSO | 2000 | 1653.73 | 67.71 |

A colorless crystal with thin long needle shape dimensions 0.5×0.05×0.05 mm³ was chosen for study. Single crystal diffraction was performed on a Bruker APEX II CCD diffractometer at room temperature with Cu Kα radiation. Oscillation photos were taken around w axis at 4φ angles. The data were indexed, integrated, and scaled with APEX software. The structures were solved and refined with the SHELX-TL package. The crystallographic data are shown in Table 2.

TABLE 2

Cystal data for compound 1

| | |
|---|---|
| Temperature | 298 K |
| Wavelength | 1.54178 Å |
| Crystal system | orthorhombic |
| Space group | P2$_1$2$_1$2$_1$ |
| Unit cell dimensions | a = 4.4317(2) Å   α = 90°. |
| | b = 13.4692(6) Å   β = 90°. |
| | c = 28.9709(13) Å   γ = 90°. |
| Volume | 1729.32(13) Å³ |
| Z | 4 |
| Density (calculated) | 1.388 Mg/m³ |
| Absorption coefficient | 1.806 mm$^{-1}$ |
| F(000) | 752 |
| Crystal size | 0.50 × 0.05 × 0.05 mm³ |
| Theta range for data collection | 3.05 to 52.98°. |
| Index ranges | −4 <= h <= 4, −13 <= k <= 13, −29 <= 1 <= 29 |
| Reflections collected | 9497 |
| Independent reflections | 2007 [R(int) = 0.0210] |
| Completeness to theta = 52.98° | 99.8% |
| Max. and min. transmission | 0.9151 and 0.4654 |
| Refinement method | Full-matrix least-squares on F² |
| Data/restraints/parameters | 2007/0/237 |
| Goodness-of-fit on F² | 0.512 |
| Final R indices [I > 2sigma(I)] | R1 = 0.0217, wR2 = 0.0629 |
| R indices (all data) | R1 = 0.0237, wR2 = 0.0666 |
| Absolute structure parameter | 0.035(17) |
| Largest diff. peak and hole | 0.094 and −0.126 e · Å$^{-3}$ |

EXAMPLE 3

Salt Formation of Compound 1

The free base of compound 1 was dissolved in ethanol to make a solution of 0.02 mmol/mL concentration. Base and acid solutions were added to separate vials containing the solution and the solvents were then evaporated at room temperature under vacuum (4 mmHg pressure). 2-Propanol (IPA) and ethanol were individually added to separate vials to re-dissolve the solids and crystallization of the solid in each vial was attempted by slow evaporation at room temperature. The resulted solids were characterized by X-ray diffraction studies. The results are shown in Table 3.

TABLE 3

| Acid solution | IPA salt form | Ethanol salt form |
|---|---|---|
| hydrochloric acid | amorphous | amorphous |
| sulfuric acid 2:1 molar ratio | Crystalline salt | Crystalline salt |
| p-toluenesulfonic acid | amorphous | amorphous |
| Free base | Crystalline FB | Crystalline FB |
| methanesulfonic acid | amorphous | amorphous |
| benzenesulfonic acid | Crystalline salt | amorphous |
| maleic acid | amorphous | amorphous |
| L-proline | amorphous | amorphous |
| phosphoric acid | Crystalline salt | Crystalline salt |
| L-aspartic acid | Crystalline FB | Crystalline FB |
| L-glutamic acid | amorphous | Crystalline FB |
| L-(+)-tartaric acid | amorphous | amorphous |
| fumaric acid | Crystalline FB | Crystalline FB |
| citric acid | amorphous | amorphous |
| D-glucuronic acid | amorphous | amorphous |

Biological Assay of Compound 1

EXAMPLE 4 c-Met Kinase Inhibition Assay

Compound 1 was screened for its ability to inhibit c-Met kinase using a standard radiometric assay. Briefly, in this kinase assay the transfer of the terminal $^{33}$P-phosphate in $^{33}$P-ATP to substrate polyE4Y is interrogated. The assay was carried out in 96-well plates to a final volume of 100 µl per well containing 0.5 nM c-Met, 100 mM HEPES (pH 7.5), 10 mM $MgCl_2$, mM NaCl, 0.01% BSA, 1 mM DTT, 0.5 mg/mL polyE4Y, and 35 µM ATP. Accordingly, compounds of the invention were dissolved in DMSO to make 10 mM initial stock solutions. Serial dilutions in DMSO were then made to obtain the final solutions for the assay. A 1.5 µl aliquot of DMSO or inhibitor in DMSO was added to each well, followed by the addition of $^{33}$P-ATP, and finally the addition of c-Met and polyE4Y (obtained from Sigma). After 20 min, the reaction was quenched with 50 µL of 30% trichloroacetic acid (TCA) containing 4 mM ATP. The reaction mixture was transferred to the 0.66 mm GF filter plates (Corning) and washed three times with 5% TCA. Following the addition of 50 µL of Ultimate Gold™ high efficiency scintillant (Packard Bioscience), the samples were counted in a Packard TopCount NXT Microplate Scintillation and Luminescence Counter (Packard BioScience). The $K_i$ values were calculated using Microsoft Excel Solver macros to fit the data to the kinetic model for competitive tight-binding inhibition. The $K_i$ for compound 1 is 0.024+/−0.008 µM.

EXAMPLE 5

Inhibition c-Met Activity in Snu5 Gastric Carcinoma Cells

Compound 1 was also screened for their ability to inhibit the Luciferase-induced signal in an engineered Snu5 cell line. Snu5 [obtained from American Type Culture Collection (Catalog number CRL-5973)] is a human gastric carcinoma known to overexpress c-Met, which is constitutively active. The cell line was transduced with the retrovirus, pCLPCX, which contains a genetic construct consisting of 6×AP1 promoter response elements and a luciferase gene having a C-terminal PEST sequence (proteolytic signal from mouse ornithine decarboxylase, which reduces the half-life of the luciferase). The constitutively active c-Met activates cellular pathways (principally MAP kinase), resulting in AP-1-induced transcription of luciferase-PEST and translation into the final product, the activity of which is quantifiable as a chemiluminescent readout upon the addition of luciferin (Steady-Glo from Promega.). Residual luminescence is strongly correlated to the inhibition of c-Met. A stable cell line was obtained by selecting the new cell line (Snu5-AP1-Luc-Pest) with puromycin. The cells were grown in complete media [Iscove's media (Invitrogen) containing 10% fetal bovine serum (FBS, Hyclone) and penicillin/gentamycin (Invitrogen)]. Compounds of the invention were dissolved in DMSO to make 10 mM initial stock solutions. Serial dilutions in DMSO were then made and transferred to complete medium to make a 10× solution. The Snu5-AP1-Luc-Pest cells were counted and diluted to 200,000-cells/mL solution. The cells (90 µL) were added to each well in a 96-well black with clear bottom plate (Costar). Then 10 µL of the 10× compound solution was added to the cells in triplicate. The plates were incubated in a 37° C./5% $CO_2$ incubator. After 6 hours, 50 µL of the Steady-Glo reagent (Promega) was added to each well and placed on a plate shaker for 5 minutes to ensure that the cells were completely lysed. The plate was read on a 1450 Microbeta Liquid Scintillation and Luminescence Counter (Perkin-Elmer). The $IC_{50}$ was calculated using a 4-parameter fit using the graphing software Prism (GraphPad). The $IC_{50}$ for compound 1 is 0.023+/−0.012 µM.

EXAMPLE 6 hERG Inhibition Assay

The cardiac potassium channel, hERG, is responsible for a rapid delayed rectifier current ($I_{Kr}$) in the human ventricle Inhibition of $I_{Kr}$ is the most common cause of cardiac action potential prolongation by non-cardiac drugs. Increase action potential duration causes prolongation of the QT interval that has been associated with a dangerous ventricular arrhythmia, torsade de pointes. hERG binding was determined using a hERG block comparative study to evaluate the effect of a given test compound on cloned hERG channels expressed in mammalian cells. See, e.g., Brown and Rampe, *Pharmaceutical News* 7, 15-20, 2000; Rampe et al., *FEBS Lett.*, 417, 28-32, 1997; Weirich and Antoni, *Basic Res. Cardiol.* 93 (Suppl. 1), 125-132, 1998; and Yap and Cain, *Clin. Exp. Allergy*, 29 (Suppl 3), 174-181, 1999.

Test compounds were delivered in HEPES-buffered physiological saline (HB-PS)+0.3% dimethyl sulfoxide (DMSO). Each test compound was applied to human embryonic kidney cells (HEK293 obtained from ChanTest Corp., Cleveland Ohio) expressing hERG (n≧3, where n=the number of cells) at concentrations sufficient to determine an $IC_{50}$. Cells were exposed to the test compound for the time necessary to reach steady-state block, but not longer than 10 minutes. The positive control (90 nM cisapride) was applied to two cells (n≧2). The hERG-exposed cells were then transferred to the recording chamber and superfused with HB-PS solution. The pipette solution for whole cell recordings included potassium aspartate (130 mM), $MgCl_2$ (5 mM), EGTA (5 mM), ATP (4 mM), and HEPES (10 mM) at a pH adjusted to 7.2 with KOH. Onset and steady state block of hERG current due to the test compound were measured using a pulse pattern with fixed amplitudes (depolarization: +20 mV for 2 seconds; repolarization: −50 mV for 2 seconds), repeated at 10 second intervals, from a holding potential of −80 mV. Peak tail current was measured during the 2 second step to −50 mV. A steady state was maintained for at least 30 seconds before applying the test compound or positive control compound. Peak tail currents were measured until a new steady state was achieved.

Data were acquired and analyzed using the suite of pCLAMP (Version 8.2) programs (MDS-AT, Sunnyvale, Calif.). Briefly, the steady state obtained before and after compound application was used to calculate the percentage of current inhibited at each concentration. Concentration-response data were fit to the following equation:

$$\% \text{ inhibition} = \{1 - 1/[1+([\text{Conc}]/IC_{50})^N]\} * 100, \text{ where}$$

[Conc] is the concentration of each compound solution tested, $IC_{50}$ is the concentration of the test compound producing half-maximal inhibition, N is the Hill coefficient, and % inhibition is the percentage of hERG potassium current inhibited at each compound concentration. Non-linear least squares fits were solved with the Solver add-in for Microsoft Excel 2000 (Microsoft, Redmond Wash.).

It was found that compound 1 inhibited hERG with an $IC_{50}$ of 110 µM, whereas compound 2 (show below) inhibited hERG with an $IC_{50}$ of 13 µM.

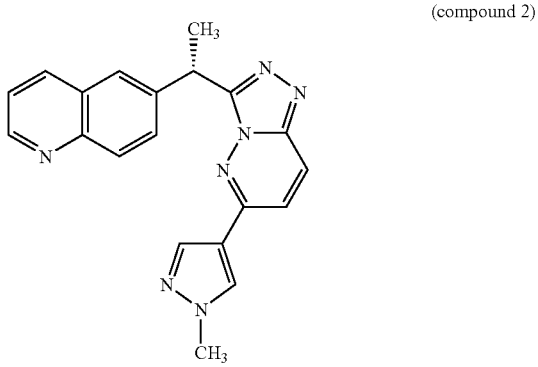

(compound 2)

EXAMPLE 7

Cytochrome P450 Inhibition Assays

The stability of compound 1 was evaluated in cDNA Baculovirus-insect cell-expressed human cytochrome P450 (CYP) isoforms CYP1A2, CYP2B6, CYP2C9, CYP2C19, CYP2D6, CYP2E1, and CYP3A4. Accordingly, the human recombinant cytochrome P450 isoforms at a final concentration of 50 pmoles of CYP/mL were incubated in phosphate buffer (pH 7.4) with 2.0 mM NADPH and compound 1 at compound concentrations of 1 µM and 10 µM. Sampling was conducted at 0 and 120 minutes and the amount of compound remaining was evaluated by LC/MS/MS analysis. The results are provided in Table 4 and are expressed as the percentage of compound remaining following a 120 minutes incubation period compared to the amount of compound present at 0 minutes (n=3 in two separate studies), along with the standard deviation (SDEV) for each study. As indicated in the tabulated results, compound 1 is metabolized by both CYP2C19 and CYP3A4 isoforms whereas compound 2 is substantially only metabolized by the CYP3A4 isoform. Challenging the CYP2C19 isoform with a higher concentration (10 µM) of compound 1 did not alter its metabolic capacities at metabolizing compound 1, suggesting a relevant capacity at metabolizing compound 1 in vivo. The in vitro results indicate that the partial metabolism of compound 1 by more than one cytochrome P450 isoform over 120 minutes would decrease the potential for drug-drug interaction with co-administered drugs in vivo.

All publications and patents cited in this specification are herein incorporated by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

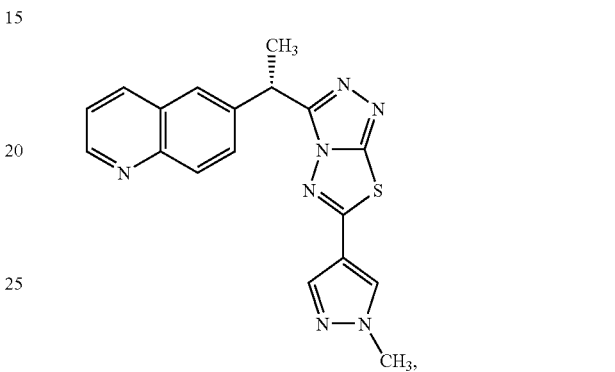

or a pharmaceutically acceptable salt thereof.

2. The compound of claim 1, wherein said compound is crystalline.

3. The compound of claim 2, wherein said compound is characterized by one or more of the following peaks in an X-ray diffraction pattern: 6.3, 9.2, 11.5, 13.3, 13.8, 14.2, 14.8, 16.2, 18.2, 18.7, and 19.8.

4. A pharmaceutical composition comprising the compound according to claim 1 or 2, or a pharmaceutically acceptable salt thereof, and a pharmaceutically acceptable carrier, adjuvant or vehicle.

5. The composition according to claim 4, additionally comprising a chemotherapeutic or anti-proliferative agent, an anti-inflammatory agent, an agent for treating atherosclerosis, or an agent for treating lung fibrosis.

\* \* \* \* \*

TABLE 4

Metabolism of Compounds 1 and 2 in human recombinant CYP isozymes

| CYP isoform (% remaining +/− SDEV) | Compound 1 (1 µM) | Compound 1 (10 µM) | Compound 2 (1 µM) | Compound 2 (10 µM) |
|---|---|---|---|---|
| CYP1A2 | 113 +/− 7.2% | 96.7 +/− 4.3% | 91.4 +/− 9.1% | 97 +/− 1.3% |
|  | 79 +/− 9.6% | 86 +/− 7.8% | 87 +/− 6.4% | 89 +/− 4.7% |
| CYP2B6 | 91.7 +/− 10.4% | 101 +/− 1.4% | 83.1 +/− 3.8% | 99.9 +/− 4.2% |
|  | 93 +/− 5.4% | 99 +/− 4.8% | 91 +/− 1.5% | 93 +/− 13.5% |
| CYP2C9 | 128 +/− 22.5% | 101 +/− 4.4% | 74.3 +/− 23.3% | 91.6 +/− 6.2% |
|  | 96 +/− 2.2% | 101 +/− 8.5% | 95 +/− 2.8% | 118 +/− 3.1% |
| CYP2C19 | 34.9 +/− 12.3% | 40.3 +/− 2.2% | 83.7 +/− 1.1% | 86.1 +/− 5.7% |
|  | 12 +/− 2.1% | 34 +/− 3.3% | 152 +/− 23.2% | 100 +/− 14.6% |
| CYP2D6 | 102 +/− 3.6% | 94.7 +/− 4.4% | 96.4 +/− 8.7% | 101 +/− 3.4% |
|  | 125 +/− 44.2% | 130 +/− 11% | 247 +/− 122% | 142 +/− 60% |
| CYP2E1 | 109 +/− 19% | 109 +/− 5.6% | 95.6 +/− 7.0% | 99.9 +/− 4.6% |
|  | 164 +/− 54.8% | 111 +/− 1.1% | 210 +/− 93.4% | 129 +/− 10.9% |
| CYP3A4 | 13.6 +/− 2.6% | 31.8 +/− 2.1% | 14.3 +/− 0.7% | 55.5 +/− 2.6% |
|  | 48 +/− 17.4% | 56 +/− 14% | 60 +/− 29% | 114 +/− 1.7% |